United States Patent
Running et al.

(10) Patent No.: US 11,589,923 B2
(45) Date of Patent: Feb. 28, 2023

(54) COMPUTER MODELING PROCEDURES FOR SURGICAL SIMULATION AND PLANNING

(71) Applicant: IMASCAP SAS, Plouzane (FR)

(72) Inventors: Donald Running, Missoula, MT (US); Jean Chaoui, Locamaria-Plouzane (FR)

(73) Assignee: IMASCAP SAS, Plouzané (FR)

( * ) Notice: Subject to any disclaimer, the term of this patent is extended or adjusted under 35 U.S.C. 154(b) by 497 days.

(21) Appl. No.: 16/489,849

(22) PCT Filed: Mar. 7, 2018

(86) PCT No.: PCT/US2018/021378
§ 371 (c)(1),
(2) Date: Aug. 29, 2019

(87) PCT Pub. No.: WO2018/165323
PCT Pub. Date: Sep. 13, 2018

(65) Prior Publication Data
US 2019/0388153 A1    Dec. 26, 2019

Related U.S. Application Data

(60) Provisional application No. 62/468,128, filed on Mar. 7, 2017.

(51) Int. Cl.
*A61B 34/10*    (2016.01)
*G16H 20/40*    (2018.01)
(Continued)

(52) U.S. Cl.
CPC .......... *A61B 34/10* (2016.02); *A61B 17/1675* (2013.01); *A61B 17/1703* (2013.01);
(Continued)

(58) Field of Classification Search
CPC ......... A61B 34/10; A61B 17/16; A61B 17/17; A61B 17/1675; A61B 17/1703; A61F 2/46; A61F 2/461; G16H 20/40; G17H 30/40
See application file for complete search history.

(56) References Cited

U.S. PATENT DOCUMENTS

| 7,715,602 B2 | 5/2010 | Richard |
| 7,857,821 B2 | 12/2010 | Couture et al. |

(Continued)

FOREIGN PATENT DOCUMENTS

| CN | 103167847 A | 6/2013 |
| CN | 105451953 A | 3/2016 |
| EP | 2471483 A1 | 7/2012 |

OTHER PUBLICATIONS

Invitation pursuant to Rule 63(1) EPC from counterpart European Application No. 18763877.0, dated Dec. 14, 2020, 4 pp.

(Continued)

*Primary Examiner* — Christopher J Beccia
(74) *Attorney, Agent, or Firm* — Shumaker & Sieffert, P.A.

(57) ABSTRACT

A system and method for streamlining inventory and ordering for certain surgical supplies. The method includes scanning, by an imaging device, a surgical site and receiving, by a processor communicatively coupled to the imaging device, data from the scan. The method also includes the processor analyzing the data, where the analyzing includes searching the data to identify predefined key features in the data that are parameters utilized by a Statistical Shape Model (SSM). The processor applies the SSM to generate a three dimensional replica of a predetermined portion of the surgical site. The processor also defines, based on the replica, at last one of: surgical planes or orientations. The processor then uti- (Continued)

lizes the replica and the surgical planes or orientations to select a solution.

27 Claims, 4 Drawing Sheets

(51) Int. Cl.
| | |
|---|---|
| *G16H 30/40* | (2018.01) |
| *A61B 17/16* | (2006.01) |
| *A61B 17/17* | (2006.01) |
| *A61F 2/46* | (2006.01) |
| *A61B 34/00* | (2016.01) |
| *A61B 90/00* | (2016.01) |
| *A61B 90/50* | (2016.01) |
| *A61B 17/56* | (2006.01) |

(52) U.S. Cl.
CPC .......... *A61B 17/1764* (2013.01); *A61F 2/461* (2013.01); *G16H 20/40* (2018.01); *G16H 30/40* (2018.01); *A61B 2017/564* (2013.01); *A61B 2034/104* (2016.02); *A61B 2034/105* (2016.02); *A61B 2034/252* (2016.02); *A61B 2090/365* (2016.02); *A61B 2090/502* (2016.02)

(56) References Cited

U.S. PATENT DOCUMENTS

| | | | |
|---|---|---|---|
| 8,147,496 B2 | 4/2012 | Couture et al. | |
| 8,506,645 B2 | 8/2013 | Blaylock et al. | |
| 9,358,114 B2 | 6/2016 | Hughes | |
| 9,375,303 B1 | 6/2016 | Cook et al. | |
| 9,980,780 B2 | 5/2018 | Lang | |
| 10,426,549 B2 | 10/2019 | Kehres et al. | |
| 10,881,462 B2 | 1/2021 | Heavener et al. | |
| 2009/0089034 A1* | 4/2009 | Penney ................ | A61B 90/36 703/11 |
| 2012/0310399 A1 | 12/2012 | Metzger | |
| 2014/0045143 A1 | 2/2014 | Berckmans, III et al. | |
| 2014/0303990 A1* | 10/2014 | Schoenefeld .......... | G16H 15/00 705/2 |
| 2015/0112659 A1* | 4/2015 | Mortier ................ | A61B 34/10 703/11 |
| 2015/0187035 A1* | 7/2015 | Hogan ............. | G06Q 10/06315 705/2 |
| 2015/0230874 A1 | 8/2015 | Musuvathy et al. | |
| 2016/0176106 A1 | 6/2016 | Staal et al. | |
| 2016/0270854 A1* | 9/2016 | Chaoui ................ | A61B 90/361 |
| 2016/0310217 A1 | 10/2016 | Park et al. | |
| 2016/0367264 A1* | 12/2016 | Geebelen ........... | A61B 17/1764 |
| 2018/0233222 A1 | 8/2018 | Daley et al. | |

OTHER PUBLICATIONS

Response to Invitation pursuant to Rule 63(1) EPC from counterpart European Application No. 18763877.0, dated Dec. 14, 2020, filed Feb. 17, 2021, 17 pp.
Office Action from counterpart Canadian Application No. 3,055,566 dated Feb. 16, 2021, 4 pp.
International Search Report and Written Opinion issued in connection with International Patent Application No. PCT/US2018/021378, 10 pages, dated Jun. 25, 2018.
Office Action from counterpart Canadian Application No. 3,055,566 dated Nov. 2, 2021, 3 pp.
Response to Communication enclosing extended European Search Report from counterpart European Application No. 18763877.0, dated Apr. 19, 2021, filed Nov. 16, 2021, 23 pp.
Communication enclosing extended European Search Report from counterpart European Application No. 18763877.0, dated Apr. 29, 2021, 13 pp.
International Preliminary Report on Patentability from International Application No. PCT/US2018/021378, dated Sep. 19, 2019, 6 pp.
Communication Pursuant to Rules 161(1) and 162 EPC dated Oct. 18, 2019 from counterpart European Application No. 18763877.0, 3 pp.
Boissonnat, J.D., "Shape Reconstruction from Planar Cross Sections," Computer Vision, Graphics, and Image Processing, vol. 44, No. 1, Oct. 1988, 29 pp.
Marker et al., "Contour-Based Surface Reconstruction using Implicit Curve Fitting, and Distance Field Filtering and Interpolation," Volume Graphics, Jan. 2006, 9 pp.
Nguyen et al., "A new segmentation method for MRI images of the shoulder joint," Fourth Canadian Conference on Computer and Robot Vision (CRV'07), May 2007, 8 pp.
Response to Office Action dated Feb. 16, 2021 from Canadian Application No. 3,055,566, filed Jun. 14, 2021, 4 pp.
First Office Action and Search Report, and translation thereof, from counterpart China (Peoples Republic) Application No. 201880030063.8 dated Apr. 1, 2022, 19 pp.
Response to Office Action dated Nov. 2, 2021, from counterpart Canadian Application No. 3,055,566 filed Mar. 1, 2022, 5 pp.
Second Office Action from counterpart Chinese Application No. 201880030063.8 dated Sep. 9, 2022, 15 pp.

\* cited by examiner

Program code in an imaging or scanning apparatus communicatively coupled to a processor scans or images a surgical site.

320

Program code receives the scan or image.

330

Program code analyzes the scan or image data by searching for predefined key identifying features in the data that are parameters utilized by a Statistical Shape Model (SSM).

340

Program code applies the SSM to the parameters to generate a replica of a predetermined location of the surgical site.

350

Program code utilizes the replica to define standard surgical planes and/or orientations.

360

Program code receives additional information.

370

Program code utilizes the replica and optionally, additional information to facilitate selection of a solution.

Program code in an imaging or scanning apparatus communicatively coupled to a processor scans or images a surgical site.

420

Program code receives the scan or image.

430

Program code to create a three dimensional replica of the bone(s), the standard planes and axis, and selects estimated sized implants and place these implants on the replica

440

Program code displays the three dimensional replica with the standard planes and axis, and then places estimated size implants in a graphical user interface of a computing device utilized by a surgeon.

450

By interacting with the replica and the additional rendering in the graphical user interface, the surgeon provides information for the program code to generate a surgical plan.

460

Program code generates, based on the plan and the replica, patient specific guides or, in the case of augmented reality, will identify the needed standard instruments for the case.

470

Program code places an order for the materials needed for the surgery.

480

Program code receives user response and as a result, accesses an ERP system.

490

Program code searches the inventory and, depending on inventory status, displays a date when the product (e.g., implant or instrument) will arrive.

COMPUTER MODELING PROCEDURES FOR SURGICAL SIMULATION AND PLANNING

REFERENCE TO RELATED APPLICATIONS

This application is a U.S. national stage application under 35 U.S.C. § 371 of International Application No. PCT/US2018/021378, filed Mar. 7, 2018, which claims the benefit of U.S. Patent Application Ser. No. 62/468,128, filed May 4, 2017, the entireties of which are incorporated herein by reference.

FIELD

The systems and methods described herein relate generally to systems and methods for simulating surgical procedures to select materials and to generate and provide enhanced data to inform surgical plans.

BACKGROUND

Stocking the materials required for a medical procedure can be expensive and inefficient because present methods do not anticipate what materials will actually be used at the time of surgery. Companies selling implants utilized for various joint-related surgeries, such as knee surgeries (e.g., total knee implants), soft tissue surgeries, and other revision surgeries do not know the exact size of the implant required for each patient in advance of a procedure. Therefore, companies that provide these supplies, including hospitals, must stock a normal distribution of inventory to cover the demand required. These inventory costs can be quite high. In addition, these companies must deliver to the operating room all of the instrumentation required to implant every size in their inventory because they do not know the actual size required to treat the patient. Along with this instrumentation is a supply of each size of their corresponding implants stored at the hospital or with their sales distributor. The lack of information regarding the actual inventory requirement for a given surgery and the need to stock excess implants at various locations is problematic and can be very expensive and require a complex logistical planning effort to coordinate implant delivery for a particular surgery.

Custom implants maybe utilized in surgeries in order to alleviate the need to order/stock multiple sizes, but this is also a non-ideal solution. Companies selling patient specific or custom implants must allocate each implant to a specific patient. If the patient cancels the surgery, which is not uncommon, the company or the hospital system must pay for the unused implant. Not only do custom implants carry higher inventory carrying costs, an added complexity to utilizing these types of implants is that there is a significant learning curve experienced by the medial professional when first using patient specific instruments and implants.

SUMMARY

Shortcomings of the prior art are also overcome and additional advantages are provided through the provision of a method for identifying an implant and procedure to be used in a medical procedure, the method includes: scanning, by an imaging device, a surgical site; receiving, by a processor communicatively coupled to the imaging device, data from the scan; analyzing, by the processor, the data, wherein the analyzing comprises searching the data to identify predefined key features in the data comprising parameters utilized by a Statistical Shape Model (SSM); applying, by the processor, to the parameters, the SSM, to generate a three dimensional replica of a predetermined location of the surgical site; defining, by the processor, based on the replica, at last one of: surgical planes or orientations; and utilizing, by the processor, the replica and the surgical planes or orientations to select an implant and/or procedure.

Systems and methods relating to one or more aspects of the technique are also described and may be claimed herein. Further, services relating to one or more aspects of the technique are also described and may be claimed herein.

Additional features are realized through the techniques described herein. Other embodiments and aspects are described in detail herein and are considered a part of the claimed invention.

BRIEF DESCRIPTION OF DRAWINGS

One or more aspects of embodiments disclosed herein are particularly pointed out and distinctly claimed as examples in the claims at the conclusion of the specification. The foregoing and objects, features, and advantages of one or more aspects of the embodiments are apparent from the following detailed description taken in conjunction with the accompanying drawing.

FIG. 3 is a workflow depicting aspects of an embodiment.

FIG. 4 is a workflow depicting aspects of an embodiment.

DETAILED DESCRIPTION

Figure 1:
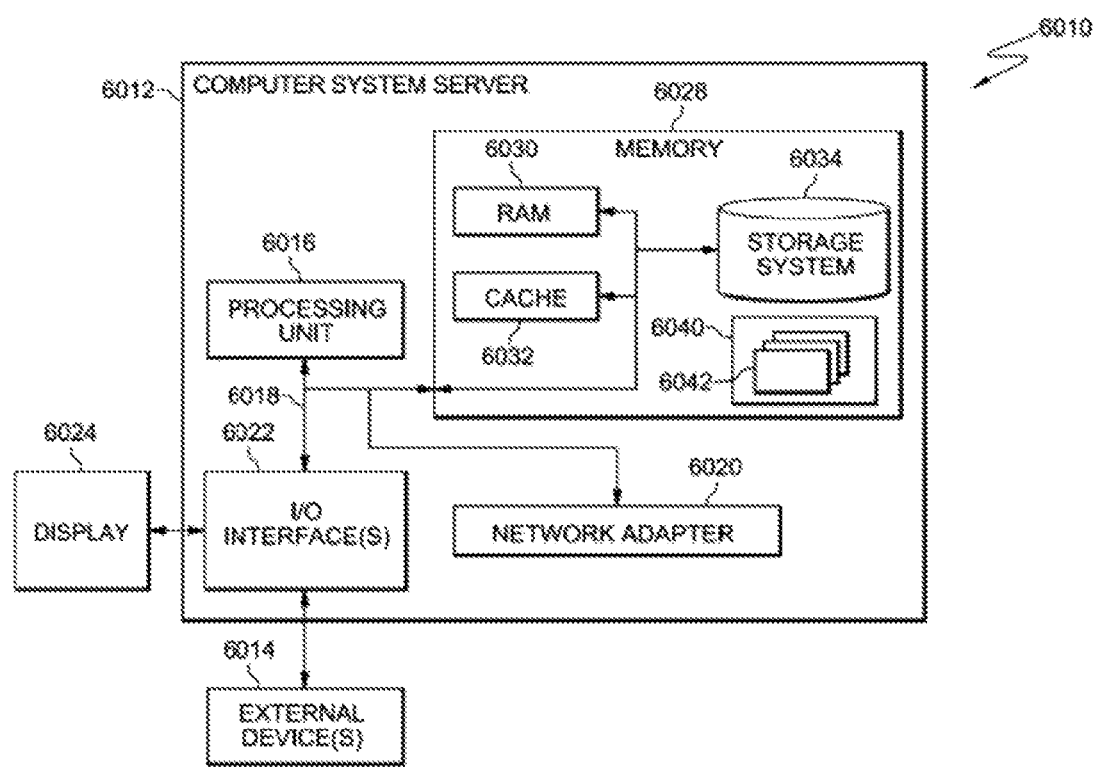
FIG. 1 depicts an embodiment of a computing node that may be utilized in an embodiment.

Aspects of the invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure. The terms software, program code, and computer code are used interchangeably throughout this application and refer to both hardware and software embodiments.

Embodiments described herein include program code that performs analysis and modeling of data obtained via Computerized Tomography (CT), Magnetic Resonance Imaging (MRI), Ultrasound scans, or equivalent medical imaging, that can be utilized for modeling. The modeling by the program code determines the size requirements for a given medial apparatus, e.g., an implant and/or accompanying instrumentation. Based on this determination, a manufacturer/supplier can produce/provide only the items (e.g., implants) required for each particular patient surgery and/or carry a reduced inventory in fewer locations, or even one central location, shipping only the needed sizes to the originator of the determination. As a result of the analysis and modeling of the digital data by the program code, the instrumentation delivered to a surgical location, such as the hospital, for each patient surgery, will only be that needed for each patient, thus introducing efficiency to this process by, for example, reducing the amount of cases and trays sterilized and carried in to an operating room. Additionally, if the manufacturer/supplier uses standard, non-patient specific implants, any unused implants would be returned to inventory to be used in future operations. By using this method, the number of non-patient specific implants offered could be increased (as in more size increments) due to the cost efficiencies realized. Thus, certain embodiments disclosed herein reduce the time cycle from surgery planning to surgery, due to the elimination of manufacturing a patient specific implant and instead utilize (a much less expensive and arguably easier to use) non-patient specific implant inventory and the need for patient specific instructions. Meanwhile, other embodiments generate parameters used for creating custom implants.

Certain embodiments provide advantages over existing solutions by eliminating much of the manual work that can lead to errors. For example, some existing software that is used to create patient specific guides for implanting standard implants, in order to operate, requires engineers to segment the bones manually and create the final three dimensional (3D) bone models. Using this software, these same engineers manually perform the virtual surgery for the surgeon and select the desired implant sizes. This takes time, money, and creates exposure to user errors. In contrast to these existing software systems, in embodiments, one or more programs automatically perform the manual work of the engineer.

Certain embodiments present advantages over existing techniques because the analysis and modeling by the computer code enables the utilization of standard (non-custom) implants, as the aforementioned determination provides the feedback necessary to select the appropriate implant that fits the requirements dictated by the program code's analysis of the digital data, without resorting to a completely custom solution and/or provide parameters utilized to generate a more accurate custom solution. In some embodiments, rather than utilize the digital data to create a custom implant, the program code analyzes and models the data in a manner that enables the program code to select an appropriate sized standard implant.

An advantage of utilizing certain embodiments disclosed herein is that based on the program code's output, health care professionals can use non-patient specific implants, as opposed to completely customized implants, and can return unused implants to inventory for future use. Based on the output received from the program code, a manufacturer/supplier can send multiple sized implants that fit the parameters generated by the program code and are therefore very close to the predicted size, for each surgery, giving the surgeon flexibility intraoperatively. The hospital may stock inventory, which can include unused supplies, and the program code can determine whether the supplies returned to inventory can be utilized for a different surgery.

Aspects of certain embodiments disclosed herein represent advances in the surgical field. Utilization of an embodiment increases the quality of surgical procedures without impacting the bottom line. Using knee arthroplasty procedures as an example, in order to perform this surgery, using existing methods, a surgical facility, such as a hospital, must stock all sizes of implants, as the size of the implant needed may not be apparent until a surgeon is engaged in surgery. Surgical supply companies are limited as to the number of implant sizes that they can offer and still command a profit, so the surgeon is always selling the best available implant from a limited number of available sizes. Investing in a custom implant for better sizing is not economically feasible in many cases. As a result of this economic reality, medial supply companies that provide instrument and implant trays generally offer anywhere from three to thirteen sizes. In an embodiment, the program code determines which implant is needed for a surgery before the surgery is performed, and can interface with an order system to place an order for that implant. Surgical centers save money when they do not have to stock multiple sizes of implants and can order only what will be needed for a given surgery. Also, because embodiments can determine the size of an implant that would provide the best solution, the program code can also measure a custom implant, allowing the program code to order a custom implant that will be utilized, and therefore, can compete cost-wise with a standard sized implant. By ordering only the implants needed for scheduled surgical procedures, surgical centers can save, for example, 50% of inventory carrying costs and manufacturers can then afford to offer more sizes of implants.

Another advantage of certain embodiments, as illustrated in FIGS. 3-4, which are discussed in detail herein, is that no industry interaction is needed until the program code places an order. Thus, embodiments eliminate both guesswork and back and forth communication that adds to the surgical cost and decreases the efficiency in this technological area.

Embodiments described herein enable the efficient recognition and delivery of size-specific, yet, sometimes, standard, instrumentation for use in surgery. For example, if augmented reality glasses are used during surgery, standard, non-patent specific instrumentation can be used by aligning the instrument cutting surfaces with the desired resection plane, as viewed through the augmented reality glasses. Delivery of size specific standard instrumentation to the surgery introduces efficiencies into the actual surgeries themselves because, based on the determination of the program code in an embodiment, unnecessary surgical equipment can be reduced or eliminated in the operating room (OR).

The utilization of embodiments described herein could increase efficiencies in orthopaedic surgery procedures around the world. For example, embodiments could increase efficiencies in every total joint surgery performed by reducing the presently large implant and instrument inventory costs and eliminating the complex and expensive logistical planning currently needed before a surgery can occur.

The embodiments described herein can be a system, a method, and/or a computer program product. As understood by one of skill in the art, aspects of the described embodiments can be implemented on one or more nodes of a computing system, which can optionally include one or more nodes of a cloud computing environment. FIG. 1 depicts an embodiment of a computing node that may include a server or other computing resource in a system into which aspects of the described embodiments are implemented. Referring now to FIG. 1, a schematic of an example of a computing node is shown. Computing node 6010 is only one example of a suitable computing node and is not intended to suggest any limitation as to the scope of use or functionality of embodiments described herein. Regardless, computing node 6010 is capable of being implemented and/or performing any of the functionality set forth hereinabove.

In computing node 6010, there is a computer system/server 6012, which is operational with numerous other general purpose or special purpose computing system environments or configurations. Examples of well-known computing systems, environments, and/or configurations that may be suitable for use with computer system/server 6012 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 6012 may be described in the general context of computer system executable instructions (referred to also as program code), such as program modules, being executed by a computer system. Generally, program modules may include routines, programs, objects, components, logic, data structures, and so on that perform particular tasks or implement particular abstract data types. Computer system/server 6012 may be practiced in distributed computing environments where tasks are performed by remote processing devices that are linked through a communications network. In a distributed environment, program modules may be located in both local and remote computer system storage media including memory storage devices.

As shown in FIG. 1, computer system/server 6012 in computing node 6010 is shown in the form of a general-purpose computing device. The components of computer system/server 6012 may include, but are not limited to, one or more processors or processing units 6016, a system memory 6028, and a bus 6018 that couples various system components including system memory 6028 to processor 6016.

Bus 6018 represents one or more of any of several types of bus structures, including a memory bus or memory controller, a peripheral bus, an accelerated graphics port, and a processor or local bus using any of a variety of bus architectures.

Computer system/server 6012 typically includes a variety of computer system readable media. Such media may be any available media that is accessible by computer system/server 6012, and it includes both volatile and non-volatile media, removable and non-removable media.

System memory 6028 can include computer system readable media in the form of volatile memory, such as random access memory (RAM) 6030 and/or cache memory 6032. Computer system/server 6012 may further include other removable/non-removable, volatile/non-volatile computer system storage media. By way of example only, storage system 6034 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 6018 by one or more data media interfaces. As will be further depicted and described below, memory 6028 may include at least one program product having a set (e.g., at least one) of program modules that are configured to carry out the functions of embodiments.

Program/utility 6040, having a set (at least one) of program modules 6042, may be stored in memory 6028 by way of example, and not limitation, as well as an operating system, one or more application programs, other program modules, and program data. Each of the operating system, one or more application programs, other program modules, and program data or some combination thereof, may include an implementation of a networking environment. Program modules 6042 generally carry out the functions and/or methodologies of embodiments as described herein.

Computer system/server 6012 may also communicate with one or more external devices 6014 such as a keyboard, a pointing device, a display 6024, etc.; one or more devices that enable a user to interact with computer system/server 6012; and/or any devices (e.g., network card, modem, etc.) that enable computer system/server 6012 to communicate with one or more other computing devices. Such communication can occur via Input/Output (I/O) interfaces 6022. Still yet, computer system/server 6012 can communicate with one or more networks such as a local area network (LAN), a general wide area network (WAN), and/or a public network (e.g., the Internet) via network adapter 6020. As depicted, network adapter 6020 communicates with the other components of computer system/server 6012 via bus 6018. It should be understood that although not shown, other hardware and/or software components could be used in conjunction with computer system/server 6012. Examples, include, but are not limited to: microcode, device drivers, redundant processing units, external disk drive arrays, RAID systems, tape drives, and data archival storage systems, etc.

A cloud computing environment, which is mentioned herein as comprising portions of a technical architecture into which aspects of the described embodiments can be implemented, can be comprised of one or more computing nodes 6010.

Figure 2:
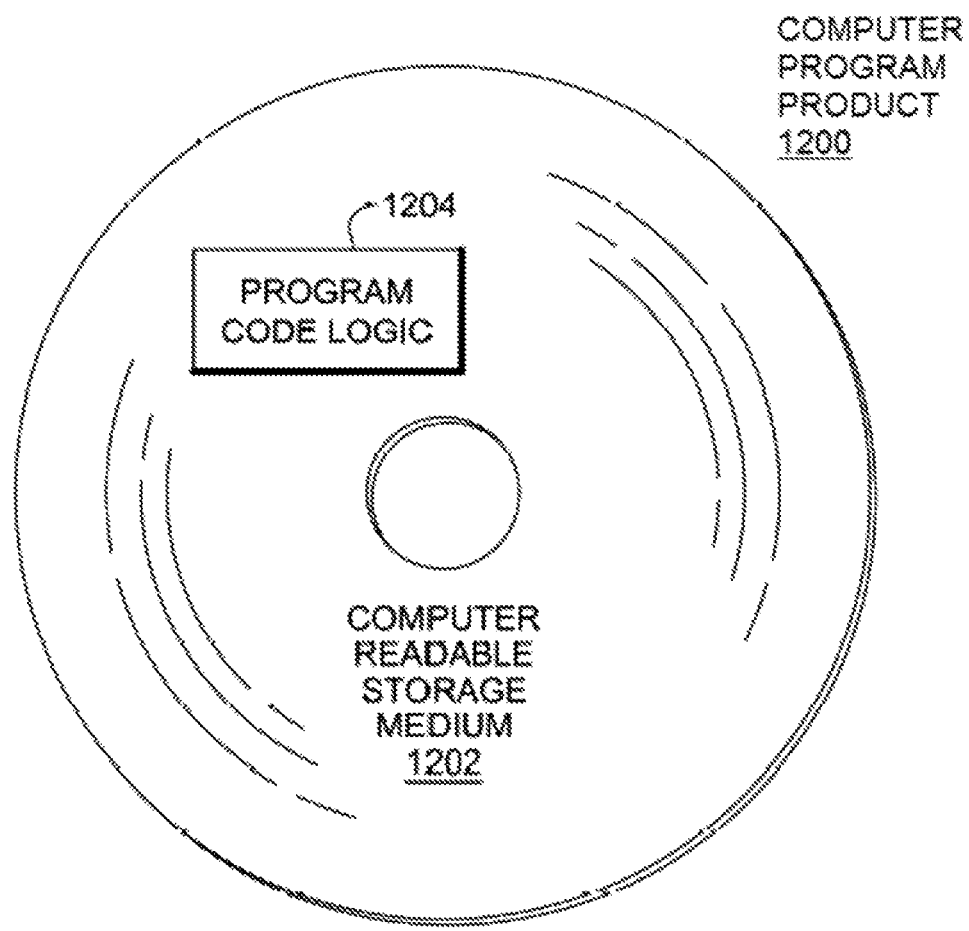
FIG. 2 depicts a computer program product that may be utilized in an embodiment.

The computer program product may include a computer readable storage medium (or media) having computer readable program instructions thereon for causing a processor to carry out aspects of the described embodiments. Referring to FIG. 2, in one example, a computer program product 1200 includes, for instance, one or more non-transitory computer readable storage media 1202 to store computer readable program code means, logic and/or instructions 1204 thereon to provide and facilitate one or more embodiments. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the described embodiments may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the described embodiments.

Certain workflows of aspects of certain embodiments are described in more details in FIGS. 3 and 4. However, referring to FIG. 1, one or more computing nodes 6010 may be utilized in the implementation of an embodiment in a computer system. For example, in an embodiment, program code that ultimately orders a medical supply (e.g., implants and/or instruments) (also called a solution herein) for a given surgical procedure may reside on a web server; computing node 6010 is an example of the technical architecture of this web server. In this example, the program code that facilitates the order may reside as a program/utility 6040 in memory 6028.

A user who wishes to interact with the program code executed, for example, by the processing unit 6016 on a web server, may connect to the web server using a personal computing device that may utilize architecture that is also similar to that of computing node 6010. Of course, in a personal computing device, such as a smartphone or tablet, the display 6024 may be integrated into the body of the device. Some of the program code can also reside as the program/utility 6040 in memory 6028 on the personal computing device. The personal computing device may connect to the web server over a communications connection, including but not limited to a virtual private network and/or the Internet.

Due to privacy concerns, patient-specific data utilized by embodiments may reside locally (e.g., in a computing node 6010 physically located at a hospital), as opposed to on the web server or another computing resource, which could conceivably be a resource of a shared cloud environment. Program code executed by a processor on the personal computing device of a user may access both the web server as well as a computing node 6010 that is local (geographically) to the user, for example, over a wired or wireless network connection.

FIG. 3 depicts a workflow diagram 300 of certain aspects of an embodiment. In an embodiment, program code in an imaging or scanning apparatus communicatively coupled to a processor, scans or images a surgical site (310) and the program code (executed by a processor) receives the resultant scan or image data (320). In an embodiment, the imaging or scanning apparatus includes, but is not limited to a CT, MM, ultrasound machine, or equivalent medical imaging device.

In some embodiments, the one or more programs may receive additional information through inputs. For example, a surgeon may take and input measurements from an initial patient visit. These measurements may include, but are not limited to, varus/valgus deformity angles, flexion contracture, hypoplastic condyles, presence and location of osteophytes, patella tracking, relevant comorbidities, age, sex, obesity, preoperative range of motion, etc.

In an embodiment, the program code analyzes the scan or image data by searching for predefined key identifying features in the data that are parameters utilized by a Statistical Shape Model (SSM) (330). In an embodiment, one or more SSM may be stored in a memory accessible to the processor and the predefined key identifying features and/or the parameters utilized by the SSM may also be retained in this or another memory accessible to the processor. In some embodiments, in addition to the image, the one or more programs may also utilize the measurements input by the surgeon, as noted above.

Based on identifying the parameters utilized by the SSM in the data, the program code applies the SSM to the parameters to generate a replica (e.g., computerized three dimensional digital model) of a predetermined location of the surgical site (340). In one example, offered for illustrative purposes only, the surgical site may be a native bone or joint and/or soft tissue, thus the program code applies the SSM to create a replica of the native bone or joint and/or soft tissue. By utilizing the SSM to create the replica, the program can create a three dimensional representation of a native bone or joint and/or soft tissue with greater than ninety-nine percent accuracy. This replica created by the program code can be utilized, as aforementioned to provide data utilized to select a surgical supply (e.g., implant or instrument) related to the area modeled, but it can also be utilized by an individual performing the surgery to guide the process.

Once the program code has generated the replica (e.g., a three dimensional computer model of a bone or joint and/or soft tissue), the program code utilizes the replica to define standard surgical planes and/or orientations (350). In an embodiment, the planes and/or orientations may include, but are not limited to, Whiteside's line, trans-epicondylar axis, posterior condylar axis, medial third of the tibial tubercle, the mechanical axis of the hip-knee-ankle, distal femoral resection plane, and/or tibial resection plane. Throughout this application, certain surgeries and certain implants are utilized as examples, however aspects of embodiments can be utilized in a wide ranges of surgeries (e.g., knee, hip, shoulder, spine), which include knee surgeries, which are discussed in more depth merely for illustrative purposes. Embodiments described herein can be utilized both for joint and soft tissue-related procedures.

In an embodiment, in addition to the scan or image data, the program code may receive additional information (360)

that it may also utilize in generating the replica and/or selecting a solution (e.g., implant) or peripheral items needed for the procedure. For example, the program code obtains user inputs on various surgical technique preferences. For example, if the femur is the surgical site, the surgeon may define how much external rotation s/he desires. If the tibia is the surgical site, the surgeon may define a tibial slope desired and a depth of resection. The user also defines solution (e.g., implant) preferences (i.e., medial pivot, posterior stabilized, cruciate retaining (CR), constrained, etc.) and, in the case of doing a non-posterior stabilized (PS) implant, whether the user wants to have a PS implant sent as a back-up. Also, the surgeon could input desired level(s) of soft tissue release on the medial or lateral side.

In an embodiment, the program code identifies and measures a variety of features that are involved in a three-dimensional computer model that it generates as well as the solution it ultimately selects. In an embodiment, the program code compares data to standard measures in the SSM, including but not limited to, bone loss. Embodiments also predict soft tissue tensioning (including in an optimization algorithm that will be discussed later) by comparing before/after surgery of soft tissue insertion points. Embodiments also calculate anticipated postoperative ranges of motion (ROMs) for the repaired joint.

The program code utilizes the replica and optionally, additional information to select the proper solution (e.g., implant) (370). For example, the program code may determine femoral and tibial implant sizes. In addition, the software may use the three dimensional data of the surgical site (e.g., bone or joint and/or soft tissue) comprised in the replica to create guides that will accurately fit to the site's surface to allow the surgeon to resect the bone and/or soft tissue in the pre-planned planar orientations (i.e., distal femur and proximal tibia). In an embodiment, the outputs of the program code related to selecting the proper solution may include, but are not limited to, an optimal range of motion based upon implant size and position, osteophyte removal and soft tissue releases, and the implant the surgeon has defined as preference, if one has been defined by a user input. In an embodiment, the program code will determine, based on the replica, one or more of: implant sizing, patient specific instrumentation (if used), recommended bone resection amounts and soft tissue releases and/or a predicted optimal range of motion. In an embodiment, the program code determines the range of motion, based, for example, on soft tissue tensioning, that can be expected based on utilization of a planned implant.

In an embodiment, an individual user may set preferences for implants, for example, PS or CR. This preference may be part of the additional information utilized by the program code to select the proper solution (370). The program code may also solicit a preferred implant solution from the user by providing the user with a choice. In an embodiment, the software displays to the user the preferences selected by a user for a given surgery and allows the user to modify and/or approve the preferences in order to verify the solution. For example, a user with a preference for a PS implant could change to a CR implant.

In an embodiment, the program code will utilize augmented reality to identify the desired resection planes with size specific instrumentation needed. In an embodiment, by utilizing augmented reality glasses, a surgeon can view not only a three dimensional picture of a surgical site, but also, a replica of the surgical site generated utilizing an SSM, which allows the surgeon to view surgical planes and/or orientations. The coupling of the view generated by the augmented reality apparatus and the model generated by the program code provide the surgeon with a surgical plan. What the surgeon views is size-specific, which allows the program code to work with the surgeon (e.g., in an iterative process), or allows the program code to select automatically the proper instruments for use in the surgery.

Utilizing augmented reality glasses during surgeries enables a surgeon to take advantage of additional aspects of an embodiment. The glasses help a surgeon formulate a surgical plan by providing a surgeon with a three dimensional view of a surgical site, based on the use of an infrared camera coupled with a model generated by an embodiment. As will be described later and illustrated by FIG. 3, in an embodiment, program code analyzes a scan or image data related to a surgical site by searching for predefined key identifying features in the data that are parameters utilized by a Statistical Shape Model (SSM). Based on these parameters, the program code constructs a replica of the site. Utilizing augmented reality glasses, a surgeon can overlay the SSM-generated replica generated by the program code in an embodiment, with the three dimensional shape of the bone and/or soft tissue, viewable using the glasses, so that the resection plane is visible to the surgeon. By overlaying these images, the surgeon is provided with the resection plane and can make resections on the plane without the need for additional instrumentation. In this manner, the augmented reality glasses provide a surgical plan with quality assurance that the surgeon is making resections at an appropriate angle.

Before surgery, in an embodiment, the program code estimates the range of possible bearing insert thicknesses to be used in the surgery. The program code utilizes the replica and virtually places implants (or other solutions) in an estimated desired position for the surgeon user. The program code renders this replica and the solution placements in a graphical user interface accessible to the processor executing the program code over a communications connection, including but not limited to, the Internet. The program code may render the graphical user interface on a personal computing device and the user can then view the replica and the placements and utilize an input device or method of the personal computing device to tweak the orientations to arrive at a final desired placement. In an embodiment, the program code can also create a digital model of the pre-resection state of the surgical site (e.g., bone or joint and/or soft tissue), which the surgeon may also view in the aforementioned graphical user interface. Viewing the pre-resection state model will help the surgeon understand the nature of the deformities and the amount of correction needed.

In one example, aspects of an embodiment can be utilized in total hip arthroplasty or replacement when an acetabular reamer is used to prepare the acetabulum to receive a replacement liner. In this procedure, the orientation and the depth of the reaming are important. When the orientation and depth of the reaming is incorrect in a surgery, the implant can fail. Some existing surgical methods provide a reamer with a laser to guide the alignment during a surgical procedure. This instrument is expensive, delicate, and will not always produce consistent results. In an embodiment, a surgeon can utilize augmented reality glasses, and the program code couples the generated model with the view of the glasses to indicate the exact alignment for the surgeon. By following the alignment indicated by the program code, a surgeon can place the hip implant correctly and will require no additional implants or orientations to correct any deficiencies in the alignment.

Even without the use of augmented reality glasses, a surgeon can view in two dimensions (and rotate for a full view), the model generated by an embodiment and utilize the model as a guide during surgery. Thus, when the program overlays the replica on an image (e.g., a CT scan) of a site, the resultant display is utilized both to determine the correct sized implant for use during a surgery and to guide the surgery procedure by providing a surgeon with a surgical plan. Appendices 1-3 include examples of view of a model generated by the program code overlaid on images of a surgical site. In each case, the program code provides a surgeon with guidance during a surgery, in addition to determining the size of an implant.

In an embodiment, the program code generates a default mock up, which the user can adjust by interacting with the program code through a graphical user interface (GUI). In an embodiment, the program code generates a default recommendation for an implant or instrument, the user interacts with the recommendation utilizing controls in a graphical user interface, the program code optimizes the recommendation with the changes implemented by the user, and the surgeon creates a surgical plan based on the optimized recommendation. The program code displays the optimized recommendation to the user as a final mockup of the surgical site, overlaid with details of the surgical plan, including the selected implants and/or instruments and planned resection orientations and amounts.

Upon identifying the solution (e.g., implant, instrumentation), the program code may communicate (over a network connection and/or within the same computer resource of the computer system) with an enterprise resource planning (ERP) system. The program code accesses the ERP system to check to see if the identified solution (e.g., femoral and tibial tray implants) is in stock. If not, the program code may initiate an order for additional inventory. If the sizes identified as the solution are not available, the program code may create an order to package the proper femoral and tibial tray implants along with the bearing inserts. In an embodiment, the program code initiates an order for any patient specific guides created in the planning or, in the use of augmented reality, and identifies the proper sized instrumentation needed for the patient. As aforementioned, the program code generates a surgical plan based on combining imaging of a surgical site with bone model it generates and this surgical plan can be sent to a surgeon along with the implants and instruments. Interacting with the ERP software, the program code can select available implant sizes that allow acceptable functional outcomes from the inventory, rather than initiating new implant orders.

FIG. 4 is a workflow diagram 400 of an embodiment that is used to illustrate how an embodiment can be utilized and provide benefits in a surgical environment where the program is being used to identify (and optionally check for the availability of, or order, the appropriate size implant and/or instrumentation). As seen in FIG. 4, program code in an imaging or scanning apparatus, communicatively coupled to a processor, scans or images a surgical site (410) and the program code receives a patient's resultant scan or image data (420). Depending upon the timing desired, the program code may store the patient data for future use or may utilize the data, upon being received by the program code, to create a three dimensional replica of the bone(s), joint and/or soft tissue, the standard planes and axis, and to select estimated sized implants and place these implants on the replica (430). The program code displays the three-dimensional replica with the standard planes and axis, and places the estimated size implants in a graphical user interface of a computing device utilized by a surgeon (440). The sizing of the recommended implants in an embodiment is more exact than existing methods. For example, in an embodiment, the program code can size implants in 1 mm increments. Through the graphical user interface rendered by the program code, the surgeon reviews (on a screen) the proposed placements, implant sizes and implant type (e.g., PS, medial pivot, CR). Through the graphical user interface, the program code accepts inputs from the surgeon as the display allows the surgeon to make changes by making user inputs, for example, clicking a button on an input device coupled to the screen displaying the replica.

The program code receives user inputs (450). For example, by manipulating the display, the surgeon can change the implant type, the femoral and tibial implant positions, the surgeon may turn on or off a display showing the pre-resection state of the bones for reference, the tibia may be rotated to a possible post-operative position to better analyze the proper tibial insert thicknesses, an estimated range of motion can be displayed, and an optimization algorithm can be used to give the surgeon the algorithm's optimal implant placement. In an embodiment, the program code displays anterior-posterior (AP) views and medial-lateral (ML) views on various planes.

Utilizing an optimization algorithm enables the program to place boundaries, providing a more customized solution. In an embodiment, the program code can change the position of the implants that it displays (450) in order to estimate postoperative flexion. For example, in an embodiment, the program code can adjust placement of an implant by three degrees and/or change a slope by three degrees, and the program code will provide the user with various permutations related to this change. In this manner, the program code determines an optimal placement.

By interacting with the replica and the additional rendering in the graphical user interface, the surgeon provides information for the program code to generate a surgical plan (450). Once the surgical plan is compete (the surgical plan may include, but is not limited to, implant type and placement), the program code generates, based on the plan and the replica, patient specific guides or, in the case of augmented reality, will identify the needed standard instruments for the case (460). In an embodiment, the patient specific guides can be created automatically and/or with some additional input from the user (e.g., surgeon) utilizing the graphical user interface, such as desired points of contact between the guide and the bone.

The appendices (1-3) provide examples of the use and generation of views for implant selection and placement in a shoulder application, by embodiments, in the surgeries of various patients. As understood by one of skill in the art, although the examples in the appendices (1-3) depict shoulders, these examples are only offered for illustrative purposes; embodiments are applicable to procedures involving all joints, knees, shoulders, hips, ankles, elbows, wrists, the spine, etc. In an embodiment, as seen in the appendices, the program code displays various views of a surgical site (from an image or scan) and the program-generated model. In the embodiment discussed in the appendices, the program code displays more than one image (e.g., three images) on a single screen of a computing device. In this example, the program code displays a first image, which is an AP view of a CT slice that the user can manipulate. The second image is an ML view of the slice. The third image is a three-dimensional model (or two dimensional model) that the program code created using the SSM. The user can overlay the AP and ML views on various planes and lines of interest, and the program code will adjust the image accordingly. For example, if the surgical site is a femur, in an embodiment, the program code enables a user to overlay the AP and ML views on the long axis of the femur. In establishing this alignment, the program code enables the user to manipulate the alignment of the lateral condyle and the medial condyle, for example, by rotating the alignment three degrees. The program code can then select and place an implant on this model at the rotation designated by the user. The program code enables the user to utilize the interface to change the implant and/or move the implant within a certain degree of freedom (e.g., six degrees). The user can also view and alter the resection plane displayed by the program code.

In an embodiment, the program code interposes soft tissues into the planning. The program code receives ultrasound data in order to render three dimensional images (e.g., replicas) that include soft tissues. For example, in a knee surgery, ultrasound data can provide the program code with information it can utilize to render the medial collateral ligament (MCL), and/or the tibial (lateral) collateral ligament (TCL), and laxity in each compartment, in the case of varus or valgus knees. The program code replicates the gradual release of ligaments.

Returning to FIG. 4, when the program code has competed its virtual creation of the plan and the patient specific guide, the program code places an order for the materials needed for the surgery (470). In an embodiment, a user can initiate the order by providing feedback, including making a selection in the graphical user interface, which the program code receives and as a result, accesses an ERP system (480).

Upon accessing the ERP system, the program code searches the inventory and, depending on inventory status, displays a date when the product will arrive (490). The program code may also create an inventory list for the company to use in packaging all the necessary components for that patient.

Aspects of embodiments prevent certain errors that are common by eliminating certain incorrect implant selections. By utilizing the model generated by the program code, a user can plan a surgery in three dimensions. Planning a surgery in three dimensions provides a surgeon with insight into a planned procedure that is not available without the model. For example, a surgeon may utilize the software described herein to plan a knee revision surgery and may gain insights from the three dimensional model generated by the software, that were unavailable in the absence of the model. For example, in a knee osteotomy, either the tibia or femur is cut and then reshaped to relieve pressure on the knee joint. In a patient with a former or previous tibial osteotomy, as part of the surgery, the surgeon may utilize a stem extension. Different offset stem extensions are available and can be classified according to four parameters: modularity, location of the offset, direction, and size of the displacement. Offset stem extensions can assist with implant alignment on the metaphysis if there is an offset diaphysis, can avoid medial-lateral or anterior-posterior component overhang, can reduce the incidence of coronal or sagittal malalignment, and can help in balancing the flexion and extension spaces by effectively translating the components. However, the program code in an embodiment may position stems in a given tibial tray in the three dimensional model and determine that the stems do not align with a tibial canal. The program code then selects a smaller tray with a stem that aligns with the canal and/or generates a patient-specific implant that accommodates the canal.

By creating the model and simulating a surgical plan, program code in an embodiment can combine patient-specific solutions (customized solutions) with solutions of standard sizes, available from vendors, including for use in the same surgical procedure. For example, in an embodiment, the program code can determine that a standard femur implant but a patient-specific tibial implant will provide the best result for a given patient. Based on this determination, the program code can place an order for each of these items.

Aspects are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions.

Aspects can be utilized in all joints, including but not limited to, knees, shoulders, hips, ankles, elbows, wrists, the spine, etc.

The appendices (1-3), are incorporated herein in their entirety for all purposes. Appendix 1, in which the first page is labeled DC 5644453, is 18 pages long. Appendix 2, in which the first page is labeled ER 5001680, is 12 pages long. Appendix 3, in which the first page is labeled WF 5746486, is 9 pages long.

Although various embodiments are described above, these are only examples. For example, computing environments of other architectures can be used to incorporate and use one or more embodiments. Further, different instructions, instruction formats, instruction fields and/or instruction values may be used. Yet further, although examples of values for abort codes and condition codes are provided, other values may be used. Moreover, different, other, and/or additional restrictions/constraints may be provided/used. Yet further, other intervals may be provided and/or used in differing ways. Many variations are possible.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or steps plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular uses contemplated.

The invention claimed is:

1. A method for a surgical plan determination for orthopedic surgery of a patient, the method comprising:

generating, by a processor, a three-dimensional replica of a predetermined portion of a surgical site utilizing a statistical shape model (SSM);

receiving, by the processor, information indicative of preference, of a surgeon who is to perform the orthopedic surgery on the patient, for at least one of one or more implants and one or more surgical procedures;

determining, by the processor, at least one of surgical planes or axes based on the three-dimensional replica;

determining, by the processor, information indicative of the surgical plan based on the three-dimensional replica of the predetermined portion of the surgical site and the information indicative of the preference, of the surgeon, for at least one of the one or more implants and the one or more surgical procedures, wherein determining the surgical plan comprises determining guides, based on the at least one of the surgical planes or axes, that fit to a surface of the surgical site for a surgeon to resect one or more of bone or soft-tissue in a preplanned planar orientation; and outputting, by the processor, to augmented reality glasses, information for the augmented reality glasses to display the three-dimensional replica and the at least one of the surgical planes or axes.

2. The method of claim 1, further comprising:
receiving, by the processor, data of a scan of the surgical site, wherein the processor is communicatively coupled to an imaging device that generates the data of the scan of the surgical site; and
searching, by the processor, the data to identify predefined key anatomic features in the data, wherein the predefined key anatomic features comprise parameters utilized by the SSM,
wherein generating the three-dimensional replica comprises applying to the parameters, the SSM, to generate the three-dimensional replica of the predetermined portion of the surgical site.

3. The method of claim 1, wherein receiving information indicative of the preference comprises receiving information indicative of the one or more surgical procedures, and wherein the information indicative of the one or more surgical procedures comprises one or more of:
a surgical technique preference;
a definition of desired external rotation of a femur;
a definition of a tibial slope and depth of resection;
a definition of preferred implants;
whether a posterior stabilized (PS) implant is needed as a back-up; or
a desired level of soft tissue release on medial or lateral side.

4. The method of claim 1, wherein the at least one of the surgical planes and axes comprise one or more of a transepicondylar axis, a posterior condylar axis, a medial third of the tibial tubercle, mechanical axis of hip-knee-ankle, distal femoral resection plane, or tibial resection plane.

5. The method of claim 1, further comprising:
determining soft tissue tensioning before and after surgery of a soft tissue insertion point; and
outputting information indicative of the soft tissue tensioning.

6. The method of claim 1, further comprising:
outputting one or more of range of motion based on implant size and position, osteophyte removal, and soft tissue releases.

7. The method of claim 1,
wherein determining information indicative of the surgical plan comprises determining, based on the three-dimensional replica, one or more of implant sizing, patient specific instrumentation, recommended bone resection amounts and soft tissue releases, and predicted optimal range of motion,
the method further comprising outputting one or more of the implant size, the patient specific instrumentation, the recommendation for bone resection amount and soft tissue releases, and the predicted optimal range of motion.

8. The method of claim 1, further comprising:
virtually placing an implant on the three-dimensional replica at an estimated desired position; and
receiving input indicative of modification to the virtual placement of the implant to arrive at a final desired placement.

9. The method of claim 1, further comprising:
accessing an enterprise resource planning (ERP) system;
determining, based on information from the ERP system, whether a determined implant is in stock; and
based on the implant not being in stock, requesting that the implant be included in the stock.

10. The method of claim 1, further comprising determining information indicative of an implant from a plurality of non-custom implants.

11. The method of claim 1, further comprising:
receiving patient characteristic information, wherein the patient characteristic information includes one or more of varus/valgus deformity angles, flexion contracture, hypoplastic condyles, presence and location of osteophytes, patella tracking, age, sex, whether the patient is obese, and preoperative range of motion,
wherein determining information indicative of the surgical plan comprises determining information indicative of the surgical plan based on the three-dimensional replica of the predetermined portion of the surgical site, the information indicative of the preference, and the patient characteristics.

12. The method of claim 1, further comprising:
determining postoperative ranges of motion (ROMs) after an implant is implanted at or near surgical site based on the surgical plan; and
outputting information indicative of the postoperative ROMs.

13. A computer system server for a surgical plan determination for orthopedic surgery of a patient, the computer system server comprising:
a memory configured to store program code; and
a processor coupled to the memory and configured to execute the program code, wherein the processor, based on execution of the program code, is configured to:
generate a three-dimensional replica of a predetermined portion of a surgical site utilizing a statistical shape model (SSM);
receive information indicative of preference, of a surgeon who is to perform the orthopedic surgery on the patient, for at least one of one or more implants and one or more surgical procedures;
determine at least one of surgical planes or axes based on the three-dimensional replica;
determine information indicative of the surgical plan based on the three-dimensional replica of the predetermined portion of the surgical site and the information indicative of the preference, of the surgeon, for at least one of the one or more implants and the one or more surgical procedures, wherein to determine the surgical plan, the processor is configured to determine guides, based on the at least one of the surgical planes or axes, that fit to a surface of the surgical site for a surgeon to resect one or more of bone or soft-tissue in a pre-planned planar orientation; and output to augmented reality glasses, information for the augmented reality glasses to display the three-dimensional replica and the at least one of the surgical planes or axes.

14. The computer system server of claim 13, wherein the processor is configured to:
receive, from an imaging device, data of a scan of the surgical site; and
search the data to identify predefined key anatomic features in the data, wherein the predefined key anatomic features comprise parameters utilized by the SSM,
wherein to generate the three-dimensional replica, the processor is configured to apply to the parameters, the SSM, to generate the three-dimensional replica of the predetermined portion of the surgical site.

15. The computer system server of claim 13, wherein to receive information indicative of the preference, the processor is configured to receive information indicative of the one or more surgical procedures, and wherein the information indicative of the one or more surgical procedures comprises one or more of:
a surgical technique preference;
a definition of desired external rotation of a femur;
a definition of a tibial slope and depth of resection;
a definition of preferred implants;
whether a posterior stabilized (PS) implant is needed as a back-up; and
a desired level of soft tissue release on medial or lateral side.

16. The computer system server of claim 13, wherein the at least one of the surgical planes and axes comprise one or more of a trans-epicondylar axis, a posterior condylar axis, a medial third of the tibial tubercle, mechanical axis of hip-knee-ankle, distal femoral resection plane, or tibial resection plane.

17. The computer system server of claim 13, wherein the processor is configured to:
determine soft tissue tensioning before and after surgery of a soft tissue insertion point; and
output information indicative of the soft tissue tensioning.

18. The computer system server of claim 13, wherein the processor is configured to:
output one or more of range of motion based on implant size and position, osteophyte removal, and soft tissue releases.

19. The computer system server of claim 13,
wherein to determine information indicative of the surgical plan, the processor is configured to determine, based on the three-dimensional replica, one or more of implant sizing, patient specific instrumentation, recommended bone resection amounts and soft tissue releases, and predicted optimal range of motion, and
wherein the processor is configured to output the one or more of implant size, the patient specific instrumentation, the recommendation for bone resection amount and soft tissue releases, and the predicted optimal range of motion.

20. The computer system server of claim 13, wherein the processor is configured to:
virtually place an implant on the three-dimensional replica at an estimated desired position; and
receive input indicative of modification to the virtual placement of the implant to arrive at a final desired placement.

21. The computer system server of claim 13, wherein the processor is configured to:
access an enterprise resource planning (ERP) system;
determine, based on information from the ERP system, whether a determined implant is in stock; and
based on the implant not being in stock, request that the implant be included in the stock.

22. The computer system server of claim 13, wherein the processor is configured to determine information indicative of an implant from a plurality of non-custom implants.

23. The computer system server of claim 13, wherein the processor is configured to:
receive patient characteristic information, wherein the patient characteristic information includes one or more of varus/valgus deformity angles, flexion contracture, hypoplastic condyles, presence and location of osteophytes, patella tracking, age, sex, whether the patient is obese, and preoperative range of motion,
wherein to determine information indicative of the surgical plan, the processor is configured to determine information indicative of the surgical plan based on the three-dimensional replica of the predetermined portion of the surgical site, the information indicative of the user preference, and the patient characteristics.

24. The computer system server of claim 13, wherein the processor is configured to:
determine postoperative ranges of motion (ROMs) after the implant is implanted at or near surgical site based on the surgical plan; and
output information indicative of the postoperative ROMs.

25. A non-transitory computer-readable storage medium storing instructions thereon that when executed cause one or more processors to:
generate a three-dimensional replica of a predetermined portion of a surgical site utilizing a statistical shape model (SSM) for orthopedic surgery of a patient;
receive information indicative of preference, of a surgeon who is to perform the orthopedic surgery on the patient, for at least one of one or more implants and one or more surgical procedures;
determine at least one of surgical planes or axes based on the three-dimensional replica;
determine information indicative of the surgical plan based on the three-dimensional replica of the predetermined portion of the surgical site and the information indicative of the preference, of the surgeon, for at least one of the one or more implants and the one or more surgical procedures, wherein the instructions that cause the one or more processors to determine the surgical plan comprise instructions that cause the one or more processors to determine guides, based on the at least one of the surgical planes or axes, that fit to a surface of the surgical site for a surgeon to resect one or more of bone or soft-tissue in a pre-planned planar orientation; and
output to augmented reality glasses, information for the augmented reality glasses to display the three-dimensional replica and the at least one of the surgical planes or axes.

26. The computer-readable storage medium of claim 25, further comprising instructions that cause the one or more processors to:
receive, from an imaging device, data of a scan of the surgical site; and search the data to identify predefined key anatomic features in the data, wherein the predefined key anatomic features comprise parameters utilized by the SSM, wherein the instructions that cause the one or more processors to generate the three-dimensional replica comprise instructions that cause the one or more processors to apply to the parameters, the SSM, to generate the three-dimensional replica of the predetermined portion of the surgical site.

27. A computer system server for a surgical plan determination for orthopedic surgery of a patient, the computer system server comprising:

means for generating a three-dimensional replica of a predetermined portion of a surgical site utilizing a statistical shape model (SSM);

means for receiving information indicative of preference, of a surgeon who is to perform the orthopedic surgery on the patient, for at least one of one or more implants and one or more surgical procedures;

means for determining at least one of surgical planes or axes based on the three-dimensional replica;

means for determining information indicative of the surgical plan based on the three-dimensional replica of the predetermined portion of the surgical site and the information indicative of the preference, of the surgeon, for at least one of the one or more implants and the one or more surgical procedures, wherein the means for determining the surgical plan comprises means for determining guides, based on the at least one of the surgical planes or axes, that fit to a surface of the surgical site for a surgeon to resect one or more of bone or soft-tissue in a pre-planned planar orientation; and means for outputting to augmented reality glasses, information for the augmented reality glasses to display the three-dimensional replica and the at least one of the surgical planes or axes.

* * * * *